(12) United States Patent
Wikler

(10) Patent No.: US 9,968,321 B2
(45) Date of Patent: May 15, 2018

(54) METHOD AND IMAGING SYSTEM FOR DETERMINING A REFERENCE RADIOGRAPH FOR A LATER USE IN RADIATION THERAPY

(71) Applicant: Ion Beam Applications S.A., Louvain-la-Neuve (BE)

(72) Inventor: David Wikler, Waterloo (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 97 days.

(21) Appl. No.: 14/975,683

(22) Filed: Dec. 18, 2015

(65) Prior Publication Data

US 2016/0174921 A1 Jun. 23, 2016

(30) Foreign Application Priority Data

Dec. 19, 2014 (EP) ..................................... 14199365

(51) Int. Cl.
*A61N 5/10* (2006.01)
*A61B 6/00* (2006.01)
*A61B 6/03* (2006.01)

(52) U.S. Cl.
CPC .............. *A61B 6/486* (2013.01); *A61B 6/032* (2013.01); *A61B 6/4085* (2013.01); *A61B 6/488* (2013.01); *A61B 6/5288* (2013.01); *A61N 5/1037* (2013.01)

(58) Field of Classification Search
CPC ............. G06T 2211/412; G06T 11/005; G06T 11/006; G06T 2211/436; G06T 2211/421; G06T 2211/424; G06T 2211/428; G06T 2211/432; A61B 6/032; A61B 6/541; A61B 6/486; A61B 6/583; A61B 6/027; A61B 6/037; A61B 6/542; A61B 6/482; A61B 6/50; A61B 5/055; A61B 6/025; A61B 6/466; A61B 6/5264; A61B 6/4085; A61B 5/08; A61B 6/06; A61B 6/12; A61B 6/5205; A61B 6/4258; A61B 6/5258; A61B 6/4266; A61B 6/4092; A61B 2034/2051; A61B 34/20; A61B 6/5288; A61B 6/4028; A61B 6/5217; A61B 5/7203; A61B 6/0457
USPC ......................................... 378/4, 5, 9, 19, 65
See application file for complete search history.

(56) References Cited

U.S. PATENT DOCUMENTS

| 9,047,701 B2 * | 6/2015 | Brehm ................. A61B 6/5235 |
| 2007/0183640 A1 * | 8/2007 | Manzke ................ G06T 11/005 382/131 |
| 2008/0281192 A1 * | 11/2008 | Keall ....................... A61B 5/08 600/426 |
| 2009/0274354 A1 * | 11/2009 | Ng ......................... A61B 6/025 382/131 |

(Continued)

*Primary Examiner* — Irakli Kiknadze
(74) *Attorney, Agent, or Firm* — Finnegan, Henderson, Farabow, Garrett & Dunner LLP

(57) ABSTRACT

Disclosed systems and methods may include an imaging system. The imaging system may include a 4D-CBCT apparatus able to generate a plurality of CBCT images corresponding to different temporal phases. The imaging system may also include a radiographic apparatus able to generate a radiograph. Further, the imaging system may include a synchronization device for correlating a radiograph of said radiographic apparatus with a CBCT image generated by said 4D-CBCT apparatus, such that a reference radiograph can be determined.

15 Claims, 3 Drawing Sheets

(56) References Cited

U.S. PATENT DOCUMENTS

| | | | |
|---|---|---|---|
| 2014/0107390 A1* | 4/2014 | Brown | A61N 5/1045 600/1 |
| 2014/0192952 A1* | 7/2014 | Keall | A61B 6/4085 378/8 |

* cited by examiner

METHOD AND IMAGING SYSTEM FOR DETERMINING A REFERENCE RADIOGRAPH FOR A LATER USE IN RADIATION THERAPY

This U.S. patent application claims priority under 35 U.S.C. § 119 to: European Patent Application No. EP14199365.9, filed Dec. 19, 2014. The aforementioned application is incorporated herein by reference in its entirety.

TECHNICAL FIELD

According to a first aspect, this disclosure relates to a method. According to a second aspect, this disclosure relates to an imaging system.

BACKGROUND

Methods for predicting motion of patient's tissues during treatment, such as for instance motion of a tumor or of an organ at risk (OAR), are desired in radiation therapy. Predicting motion or position of tissues of patients during treatment is notably necessary in order to avoid radiating OARs and/or in order to irradiate a tumour with a required dose.

Techniques have been developed for predicting a motion of a tissue during treatment. Four-Dimensional Computed Tomography (4D-CT) allows generating different CT images at different times, as it is known by the one skilled in the art. Time represents a fourth dimension, hence the adjective 'Four-Dimensional'. From the different CT images, one can deduce motions of a tissue over time. Such motions result, for instance, from a patient's breathing. By knowing these displacements, a treatment plan that takes them into account can be established. It is then assumed that motions occurring during the time 4D-CT is performed also occur and are the same during actual treatment. However, 4D-CT is generally performed well before treatment, typically one to two weeks before. Hence, 4D-CT cannot accurately represents motion of tissues during treatment. For instance, it is possible that, between the time 4D-CT is performed and the time of treatment, geometry of a tumour (its position, shape, or size for instance) has changed and/or a patient's breathing cycle has varied.

Four-Dimensional Cone Beam Computed Tomography (4D-CBCT) is another technique known by the one skilled in the art. By positioning a source and a detector of a 4D-CBCT apparatus at different angular positions around an isocenter, and by recording or computing the acquisition times at which the different CT scans or CT projections are taken or acquired, one can reconstruct 3D images (named 4D-CBCT images) of a portion of a patient positioned at said isocenter for different times. Quality of 4D-CBCT images is poorer than quality of 4D-CT images. However, 4D-CBCT presents some advantages compared to 4D-CT. In particular, 4D-CBCT can be installed in a treatment room. Hence, 4D-CBCT images can be taken just before treatment and around an isocenter where a patient is positioned during treatment. That is generally not possible with a 4D-CT procedure. In order to keep precision and quality of 4D-CT images, 4D-CBCT images are generally used in order to rescale the former. For instance, if it is determined that a tumour follows a closed path during a breathing cycle from 4D-CT images, a baseline shift is determined from 4D-CBCT. This baseline shift generally comprises a space shift between closed paths observed in 4D-CT images and 4D-CBCT images, and an amplitude variation between said closed paths. From the knowledge of this baseline shift, a patient position correction can be estimated and/or a treatment plan, based on 4D-CT images can be updated.

In general, 4D-CBCT cannot be performed during treatment. Indeed, its source and detector that need to be positioned at different angular positions are generally attached to a gantry supporting a nozzle used for treatment. When delivering a radiating treatment beam, the treatment head (a nozzle for instance) cannot be positioned at the different angular positions required for the 4D-CBCT technique. Therefore, 4D-CBCT cannot be used for monitoring a patient's tissues during treatment. In other words, 4D-CBCT cannot be used for direct tissue tracking. However, it is desired to have some knowledge on tissue position during treatment, for instance to know when to deliver the treatment beam in order to correctly irradiate a tumour while at same time not irradiating OARs. If only 4D-CT and 4D-CBCT are used, assumption of same regular, periodic respiratory motion between the time 4D-CBCT is performed and the time of treatment is generally made. This is a limitation that induces a problem of precision in the determination of a position of a tissue of a patient during treatment. Therefore, it would be desirable to have a direct method of tracking a tissue of a patient during treatment.

Direct tumor tracking methods using implanted fiducial markers have the following disadvantages. Patients may face infection pneumothorax risks or from implantation. Implanted markers may easily migrate in a patient's body. Fiducial markers can interfere with a treatment beam in particle therapy. In particular, a range of a particle beam (proton beam for instance) can be modified when it is passing through the a fiducial marker. It is therefore desirable to have a tracking method not relying on implanted markers.

Techniques not using implanted markers have been reported. During treatment, radiographs are taken at different times, by fluoroscopy for instance. In order to monitor patient's tissues, these radiographs, taken during treatment, are compared with reference radiographs that are named Digitally Reconstructed Radiographs (DRRs). Each DRR generally corresponds or refers to a given time or a given temporal phase, for instance a respiratory phase. If a radiograph taken during treatment matches with a DRR, it is then determined that the position of patient's tissues corresponds to the position of patient's tissues corresponding to the given temporal phase of the selected DRR. According to another point of view, if a radiograph taken during treatment matches with a DRR, it is then determined that said radiograph is characterized by a temporal phase equivalent to the temporal phase associated with said DRR.

For generating a DRR, a CBCT or CT image corresponding to a given temporal phase (or given time) is selected from the different images generated by a 4D-CBCT or by a 4D-CT technique. Then, this CBCT or 4D-CT image is numerically projected on a planar surface. By performing this operation for different temporal phases, one can build corresponding different DRRs.

Tissue tracking or tracking of temporal phases relying on the use of DRRs has some disadvantages. First, one needs to build the different DRRs. This requires using some mathematical operations that are sometimes complex. It takes also some time, and needs computation resources. Second, the accuracy of the result from the comparison phase between a radiograph taken during treatment and a DRR is quite poor. This is mainly due to the fact that quality of a DRR is low because it results from numerical operations of projection of a 3D image on a plane. Quality is still lower if a DRR results from a projection of a CBCT image as it is generally the case. Indeed, CBCT images are often blurred because of the motion of the gantry supporting the source and the detector of a (4D)-CBCT apparatus.

Providing a method for determining a reference radiograph other than a DRR for a later use during treatment in tissue tracking or time tracking may provide advantages over these systems and methods. In particular, having a reference radiograph that would provide a result of comparison with a radiograph taken during treatment that is more precise may improve treatments.

SUMMARY

According to a first aspect, disclosed embodiments may provide a method for determining a reference radiograph for a later use during treatment in radiation therapy, that would provide better accuracy of a later comparison result between said reference radiograph and a radiograph taken during treatment. To this end, the disclosure includes a method comprising the steps of:

i. providing a Four-Dimensional Cone Beam Computed Tomography (4D-CBCT) apparatus, comprising a source and a detector that can be positioned at different angular positions around a patient, said 4D-CBCT apparatus being able to generate a plurality of CBCT images corresponding to different times;

ii. providing a radiographic apparatus comprising a radiographic source and a radiographic detector and configured for generating a sequence of radiographs corresponding to different times;

iii. providing positioning means configured for positioning a patient for generating CBCT images of said patient with said 4D-CBCT apparatus and radiographs with said radiographic apparatus;

iv. performing a 4D-CBCT scanning sequence with said 4D-CBCT apparatus for generating a plurality of CBCT images of a portion of the patient's body, said generated CBCT images corresponding to different temporal phases associated to said patient; characterized in that the method further comprises the steps of v. performing a radiographic sequence with said radiographic apparatus so as to generate a number of radiographs of said patient, said number of radiographs corresponding to different temporal phases associated to said patient;

vi. providing a synchronization device configured for correlating a CBCT image corresponding to a given temporal phase with a radiograph corresponding to an equivalent temporal phase;

vii. correlating with said synchronization device a radiograph obtained in step v with a designated CBCT image of said CBCT images obtained in step iv, said designated CBCT image corresponding to a designated temporal phase;

viii. identifying the correlated radiograph obtained in step vii as said reference radiograph.

Therefore, the disclosure may determine a reference radiograph experimentally, and to correlate or link a radiograph with a CBCT image to determine said reference radiograph. Then, one can have better accuracy of a later comparison result between said reference radiograph and a radiograph taken during treatment. Indeed, the comparison is performed between images of similar type: with the method of the disclosure the reference radiograph is also an image resulting from experiment. In particular, when generating the reference radiograph with the method of the disclosure, there is no longer loss of information resulting from numerical operations such as a numerical operation of projection of a 3D image on a plane. The reference radiograph is more precise, and closer to the radiographs taken during treatment. Finally this allows having a higher accuracy of a later comparison result between the reference radiograph and a radiograph taken during treatment. The radiograph taken during said radiographic sequence may be generated with a same radiographic apparatus as the one used during treatment and that is used for generating different radiographs.

Numerical operations of projection of a (CB)CT image on a plane are no longer necessary with the method of the disclosure. It is therefore simpler. It also requires less computational resources. The method of the disclosure is therefore more efficient.

The method of the disclosure has other advantages. By using the method of the disclosure, it is not necessary to assume a same regular, periodic respiratory motion between the time 4D-CBCT is performed and the time of treatment. Moreover, the method of the disclosure allows implementing a tracking method of a tissue of a patient or of a gating time of treatment without the need of any implanted fiducial markers. In an embodiment, only one fluoroscopic axis of the radiographic apparatus is used for generating the reference radiograph. Then, only one fluoroscopic axis of the radiographic apparatus is also used during treatment for generating a radiograph that is compared with one or more reference radiographs. Using only one fluoroscopic axis is possible because 3D information is contained in the CBCT and CT images. In particular, two fluoroscopic axes of the radiographic apparatus are not necessary for generating the reference radiographs and the radiographs during treatment. As a result, the low dose received by a patient during the generation of the reference radiographs just before treatment and the radiographs during treatment is reduced.

In an embodiment, the reference radiograph is generated with same experimental setup (in particular with same radiographic apparatus) as the one used during treatment for generating a radiograph that is compared with said reference radiograph for tracking a patient's tissue.

As it is known by the one skilled in the art, examples of radiation therapy are: X-ray therapy (therapy using photons), and particle therapy (therapy using energetic ionizing particles such as protons or carbon ions).

The method of the disclosure is neither a surgical nor a therapeutic treatment method. In particular, the method of the disclosure has no therapeutic effect. Indeed, the maximum dose deposited by the 4D-CBCT apparatus generally varies between 1 cGy to 5 cGy. The dose deposited during one radiograph performed by the radiographic apparatus is generally of the order of few hundreds of $\mu$Gy.

The synchronization device allows correlating a CBCT image corresponding to a given temporal phase with a radiograph corresponding to an equivalent (or to same) temporal phase. A time can be associated to a CBCT image generated by the 4D-CBCT apparatus. A time can also be associated to a radiograph generated by the radiographic apparatus. For the latter, this time represents for instance a time of acquisition. From the time associated with a CBCT image, one can define an associated temporal phase. A temporal phase generally corresponds to a time interval with a low limit and a high limit. From the time associated with a radiograph, one can also define an associated temporal phase. Thereafter, the two temporal phases are compared. Equivalent temporal phases mean that the two temporal phases do not need to be exactly the same for associating a radiograph with a designated CBCT image, even if for an embodiment, the correlated radiograph as same temporal phase as the designated CBCT image. For instance, one can quality a temporal phase to be equivalent to another one if their low and high limits are the same within 10%, in an embodiment, within 5%. When dealing with cyclic functions such as cyclic motions or organs or tumours, for instance a respiratory cycle, one can have two different temporal phases that are nevertheless equivalent. Indeed, in a cyclic function has a time period T. Two different temporal phases are equivalent if they are separated by a multiple of said time period T.

In step iv, the plurality of CBCT images is generated for instance from different operations applied to a plurality of CBCT scans or CBCT projections. Such operations are known by the one skilled in the art. In an embodiment, a CT image (3D image) is associated to each temporal phase of step iv. The correlated radiograph of step vii thus has same or equivalent temporal phase as the one of the designated CBCT image.

In an embodiment, the radiographic sequence of step v is performed during at least a (temporal) portion of the 4D-CBCT scanning sequence of step iv. According to this embodiment, disclosed embodiments may perform a radiographic sequence simultaneously to a 4D-CBCT scanning sequence, generally just before treatment. Then, no additional time is necessary to build numerical reference radiographs such as DRRs. The method of the disclosure is therefore more efficient. According to another possible embodiment, the radiographic sequence and the 4D-CBCT scanning sequence are performed sequentially.

In an embodiment, the different temporal phases of step iv and step v correspond to different respiratory phases of a respiratory cycle. In an embodiment, said respiratory cycle is the respiratory cycle of said patient. A respiration phase could be named a respiratory portion of a respiratory cycle.

In an embodiment, each of said CBCT images of step iv corresponds to a CT image generated previously by a CT apparatus. That means that each CBCT image then corresponds to a CT image such that both images correspond to a same or equivalent temporal phase, for instance to a same or an equivalent respiratory phase In an embodiment, in that in step vii, multiple radiographs obtained in step v are correlated with multiple designated CBCT images such that in step viii multiple reference radiographs are identified, each of said multiple reference radiographs corresponding to a given designated temporal phase.

In an embodiment, ten or more (for instance, 11, 12, 13, 14, 15) CBCT images corresponding to ten or more (for instance, 11, 12, 13, 14, 15) different temporal phases are generated from the 4D-CBCT scanning sequence of step iv.

In an embodiment, at least ten radiographs for at least ten different phases are generated from the radiographic sequence of step v, and at least ten reference radiographs are determined. For instance, 11, 12, 13, 14, or 15 radiographs are generated from the radiographic sequence of step v, and 11, 12, 13, 14, or 15 reference radiographs are determined.

Embodiments also include a method for determining during treatment a position of a tissue of a patient in radiation therapy comprising the steps of:
  A. providing a reference radiograph that has been determined by a method as presented above;
  B. providing a radiographic apparatus comprising a radiographic source and a radiographic detector;
  C. positioning a target volume of the patient's body between the radiographic source and the radiographic detector of the radiographic apparatus of step B;
  D. generating a radiograph of a target volume of the patient's body with the radiographic apparatus of step B;
  E. comparing the radiograph generated in step D with the reference radiograph of step A.;
  F. if the radiograph of step D is sufficiently close to the reference radiograph of step A, determining a position of a tissue of said patient during step D from the CBCT image correlated with said reference radiograph.

In an embodiment, the radiographic apparatus of step B is the same as the radiographic apparatus used for determining the one or more reference radiographs.

Disclosed embodiments also include a method for helping deciding when to send a treatment beam to a patient in radiation therapy and comprising the steps of:
  A. providing a reference radiograph corresponding to a given temporal phase for which it is desired to send said treatment beam, said reference radiograph being determined by a method according to first aspect of the disclosure;
  B. providing a radiographic apparatus comprising a radiographic source and a radiographic detector configured for imaging a patient during treatment;
  C. positioning a target volume of the patient's body in treatment position;
  D. generating a radiograph of a target volume of the patient's body with the radiographic apparatus of step B;
  E. comparing the radiograph of step D with the reference radiograph of step A;
  F. if the radiograph of step D is sufficiently close to the reference radiograph of step A, determining that said treatment beam should be sent to said patient.

In an embodiment, the radiographic apparatus of step B is the same as the radiographic apparatus used for determining the one or more reference radiographs.

Different respiratory phases of a patient can be determined by a spirometer for instance.

In an embodiment, the duration of the 4D-CBCT scanning sequence of step iv is comprised between four and eight respiratory cycles. A respiratory cycle is generally defined as comprising one breath in phase, and one breath out phase. Other definitions could nevertheless be used.

In an embodiment, the duration of the 4D-CBCT scanning sequence of step iv is comprised between one and three minutes.

In an embodiment, the duration of the radiographic sequence of step v is comprised between one and two respiratory cycles.

In an embodiment, the duration of the radiographic sequence of step v is comprised between fifteen seconds and one minute.

According to a second aspect, the disclosure relates to an imaging system for identifying a reference radiograph for use in radiation therapy, said imaging system comprising:
  i. a 4D-CBCT apparatus comprising a source and a detector that can be positioned at different angular positions around a patient, said 4D-CBCT apparatus being able to generate a plurality of CBCT images corresponding to different times;
  ii. a radiographic apparatus comprising a radiographic source and a radiographic detector and configured for generating a sequence of radiographs corresponding to different times; and iii. a synchronization device for correlating a CBCT image corresponding to a given temporal phase with a radiograph corresponding to an equivalent temporal phase, such that the correlated radiograph can be identified as a reference radiograph.

The advantages mentioned for the method of the disclosure apply to the imaging system, mutatis mutandis. The different embodiments presented for the method of the disclosure apply to the imaging system, mutatis mutandis.

In an embodiment, said CBCT images generated with said 4D-CBCT apparatus are three dimensional images and said radiographs generated with said radiographic apparatus are two dimensional images.

In an embodiment, said synchronization device comprises control means (for instance a controller, a microcontroller, or any other types of controller) for controlling said radiographic apparatus for performing a radiographic sequence for generating a radiograph corresponding to an equivalent (or the same) temporal phase as the temporal phase associated with a CBCT image generated by said 4D-CBCT apparatus, such that a reference radiograph can be determined. In an embodiment, control means is programmed for controlling said radiographic apparatus for performing a radiographic sequence for generating a radiograph corresponding to an equivalent (or the same) temporal phase as the temporal phase associated with a CBCT image generated by said 4D-CBCT apparatus.

In an embodiment, said control means is able to control said radiographic apparatus for performing a radiographic sequence during at least a portion of a 4D-CBCT scanning sequence of said 4D-CBCT apparatus for generating said radiograph.

In an embodiment, the said synchronization device is able to determine a temporal phase of a CBCT image.

BRIEF DESCRIPTION OF THE DRAWING

These and further aspects of the disclosure will be explained in greater detail by way of example and with reference to the accompanying drawings in which.

The drawings of the figures are neither drawn to scale nor proportioned. Generally, identical components are denoted by the same reference numerals in the figures.

DETAILED DESCRIPTION

Figure 1:
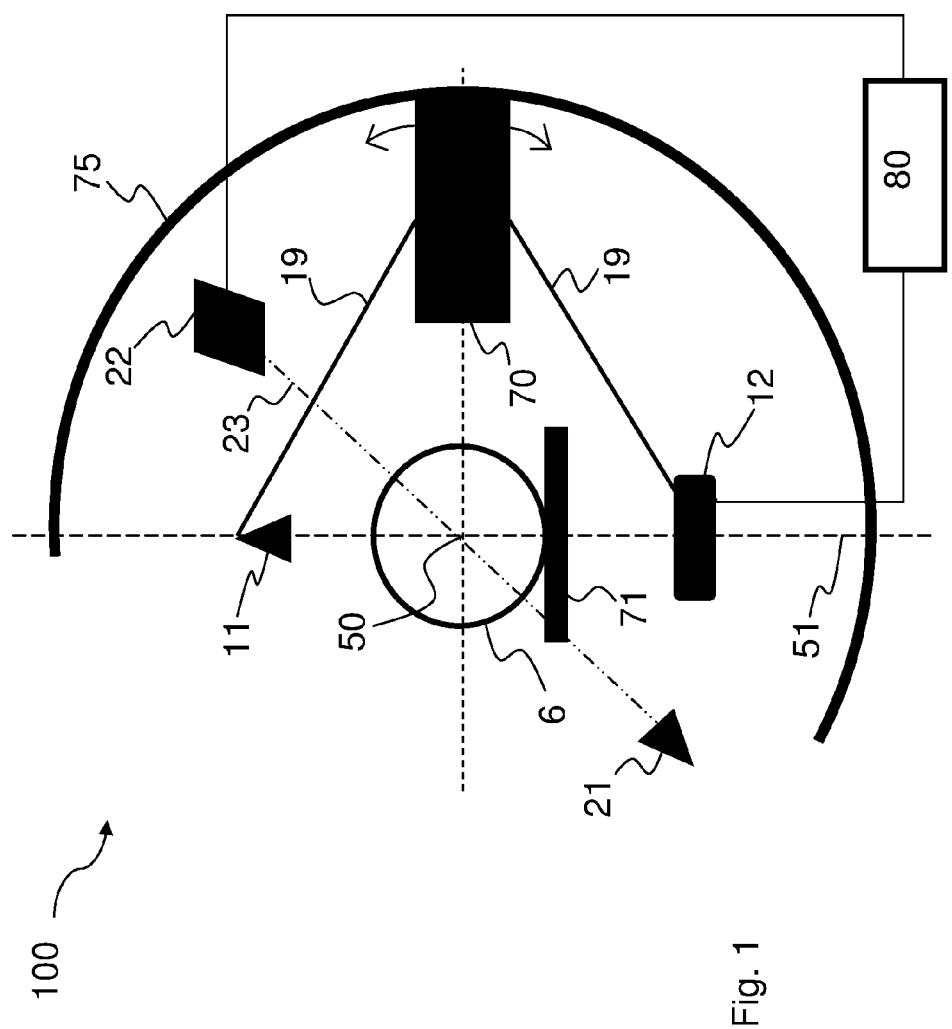
FIG. 1 shows an example of an imaging system according to the disclosure.

FIG. 1 shows an example of an imaging system 100 according to the disclosure. It comprises a Four-Dimensional Cone Beam Computed Tomography (4D-CBCT) apparatus. This 4D-CBCT apparatus comprises a source 11 and a detector 12 that can be positioned at different angular positions 51 around a patient 6. As an example, an X-Ray Tube of max 150 kV could be used for the source 11, and a Flat Panel Digital Radiography Detector (aSi with CsI scintillator) could be used for the detector 12. Other types of source 11 and detector 12 could nevertheless be used. The patient 6 is generally located at a so-called isocenter 50. The CBCT apparatus is an X-ray CBCT apparatus using X-rays for producing CBCT images 15. Then, the source 11 is an X-rays source, and the detector 12 is an X-rays detector. Other types of CBCT apparatus could nevertheless be used.

In an embodiment, the source 11 and detector 12 of the 4D-CBCT apparatus are mounted on a nozzle 70, for instance by the intermediate of arms 19. In an embodiment, said nozzle 70 is part of an apparatus used for radiation therapy, such as for instance particle therapy. As it is known by one skilled in the art, a nozzle 70 is then used for sending and directing a radiating beam towards a portion of a patient 6. In an embodiment, the nozzle 70 is mounted on a gantry 75 for helping positioning the nozzle 70 at different angular positions 51 around an isocenter 50. When source 11 and detector 12 of the 4D-CBCT apparatus are coupled to the nozzle 70, they can be placed at different angular positions 51 by positioning the nozzle 70 at different angular positions 51 along the gantry 75. With reference to FIG. 1, the different angular positions 51 of source 11 and detector 12 of the 4D-CBCT apparatus are in the plane of said FIG. 1.

As it is known by the one skilled in the art, a 4D-CBCT apparatus allows generating different CBCT images 15 for different times, or for different temporal phases. By positioning the source 11 and the detector 12 at different angular positions 51 around the isocenter 50, and by recording the time at which different CT scans 13 are taken with the 4D-CBCT apparatus at different angular positions 51, one can reconstruct, for different times, 3D images (named 4D-CBCT images 15) of a portion of a patient 6 positioned at the isocenter 50. Positioning means 71 allows positioning the patient 6 at the isocenter 50. Different examples or positioning means 71 are possible, as it is known by the one skilled in the art. According to a first example, positioning means 71 comprises a table onto which a patient 6 can lie. In an embodiment, this table can move, for instance can rotate and/or can translate vertically. Other examples of positioning means 71 are nevertheless possible.

The 4D-CBCT apparatus 10 is being able to generate a plurality of CBCT images 15 corresponding to different temporal phases. The temporal phases are for example the temporal phases of a respiratory cycle 90 of a patient 6. The temporal phases could represent other physiological phases of a patient 6. For instance, the temporal phases could represent temporal phases corresponding to different positions of an organ of a patient 6 over time, such as the different positions of a heart of a patient 6.

In addition to the 4D-CBCT apparatus, the imaging system 100 also comprises a further radiographic apparatus for generating radiographs 25 of a patient 6. The radiographic apparatus comprises a radiographic source 21, and a radiographic detector 22. In an embodiment, the radiographic apparatus allows performing fluoroscopy that is known by one skilled in the art. Radiographic source 21 may be an X-ray source, and radiographic detector 22 may be an X-ray detector. Examples of commercial X-ray detectors 22 are: Varian 4030CB, 4040D, Thales Pixium 4343RF, and Perkin Elmer XRD 1621. In an exemplary configuration, the radiographic axis 23 between radiographic source 21 and radiographic detector 22 is out of the plane of FIG. 1. Then, the angle between radiographic axis 23 and plane of FIG. 1 may be equal to 45°. In another example, the radiographic axis 23 can be in the plane of FIG. 1.

The radiographic apparatus could comprise more than one radiographic source 21, and more than one radiographic detector 22. For instance, the radiographic apparatus 20 could comprise two radiographic imaging pairs, each pair comprising one radiographic source 21, and one radiographic detector 22. Then, the radiographic axes 23 of the two radiographic imaging pairs may be positioned at an angle comprised between 45° and 75° with respect to each other, and may be at an angle of 60°. In another example using two detectors, the radiographic axes 23 are configured for obtaining two orthogonal image pairs. With the radiographic apparatus, two dimensional images of a part of the body of a patient 6 can be obtained. The radiographic apparatus is configured for taking a series of images as function of time and hence generating a sequence of radiographs corresponding to different temporal phases. In this way, one can obtain two dimensional images at different moments in time or at different temporal phases of a cyclic function such as for example different temporal phases of the respiratory cycle of a patient 6. The radiographic apparatus is therefore for instance a fluoroscopy machine.

Examples of measurement parameters for 4D-CBCT are as follows, only for illustrative purposes (the disclosure is not limited to these experimental parameters). Source 11 and detector 12 of CBCT apparatus can rotate at the followings rotation speeds: 0.5 or 1 RPM. 600 to 900 projections (or CBCT scans 13) can be taken during a rotation for instance.

The imaging system 100 also comprises a synchronization device 80. It allows correlating one or more CBCT images 15 with one or more radiographs 25 of a sequence of radiographs taken with the radiographic apparatus discussed above. Then, one radiograph 25 obtained at a given temporal phase can be correlated with one CBCT image 15 obtained at same or equivalent temporal phase. As discussed before, a temporal phase can be for instance a temporal phase of a respiratory cycle 90 of a patient 6. Different embodiments of the synchronization device 80 are possible for obtaining such a correlation. For instance, the synchronization device 80 can be a computing unit included in a treatment planning system. According to another example, the synchronization device 80 is an independent computer or an independent computing module able to communicate with a 4D-CBCT apparatus and with a radiographic apparatus. The synchronization device 80 could also be an element of the 4D-CBCT apparatus, or of the radiographic apparatus.

A radiographs 25 obtained with the radiographic apparatus can be correlated with a designated CBCT image 15 of the multiple CBCT images 15 obtained with the 4D-CBCT apparatus. The designated CBCT image 15 corresponds to a designated temporal phase. This designated CBCT image 15 can be for example an image where it is observed that the target volume is located in a position where it is safe to be irradiated. The correlated radiograph can then be identified as being a reference radiograph 35. This reference radiograph 35 can then be used in a later treatment phase and be compared with a radiograph taken during the treatment session. Based on the comparison with the reference radiograph 35, it can be decided if a treatment beam should be or could be sent to the target volume or not. Based on the comparison between a reference radiograph 35 and the actual image taken during the treatment session a gating signal for gating the treatment beam can be determined for instance. In another example, from a multiple number of CBCT images 15 one can designate a multiple number of images for which the target volume is well located for irradiating. Different radiographs 25 obtained with the radiographic apparatus can thereafter be correlated with these different designated CBCT images 15, for obtaining a plurality of reference radiographs 35. In this case, one (or more) radiograph 25 taken during treatment can be compared with such multiple reference radiographs 35 for taking a decision to send the treatment beam to the patient 6 or not.

According to a possible embodiment, the synchronization device 80 comprises a clock. Then, it can attribute temporal information to CBCT images 15 reconstructed from CBCT scans 13, and to radiographs 25 generated by the radiographic apparatus. For instance, it can assign to a CBCT image 15 and to a radiographs 25 a temporal phase. After, one can link or correlate a radiograph 25 with a CBCT image 15 if they have same or similar temporal phase.

According to another possible embodiment, the synchronization device 80 is able to analyze a CBCT image 15 for attributing it a temporal phase. This is notably possible when a temporal phase represents a respiratory phase of a respiratory cycle. Indeed, by analyzing different CBCT images 15 taken over time, it is possible to attribute to each of them a respiratory phase of a respiratory cycle. Then, the device 80 may be also able to analyze a radiograph 25 for attributing it a temporal phase. This is also notably possible when a temporal phase represents a respiratory phase of a respiratory cycle. As for CBCT images 15, by analyzing different radiographs 25 taken over time, it is possible to attribute to each of them a respiratory phase of a respiratory cycle. Knowing the temporal phases of CBCT images 15 and of radiographs 25, it is then possible to link or correlate CBCT images 15 and of radiographs 25 having same or similar temporal phases.

According to another possible embodiment, the synchronization device 80 has a clock but also comprises means for monitoring breathing of a patient 6 (for instance, a spirometer). Then, by recording the times at which CBCT scans 13 are taken, one can attribute to reconstructed CBCT images 15 respiratory phases. Also, by recording the times at which radiographs 25 are taken, one can associate to each radiograph 25 a respiratory phase. Finally, the device can synchronize or correlate CBCT images 15 and radiographs 25 having same respiratory phase.

It is also possible that for CBCT images 15, image processing is used for determining a temporal phase associated to each CBCT image 15, and that for radiographs 25, a device such as a spirometer is used for associating a respiratory phase to each of them. The opposite is also possible.

Figure 2:
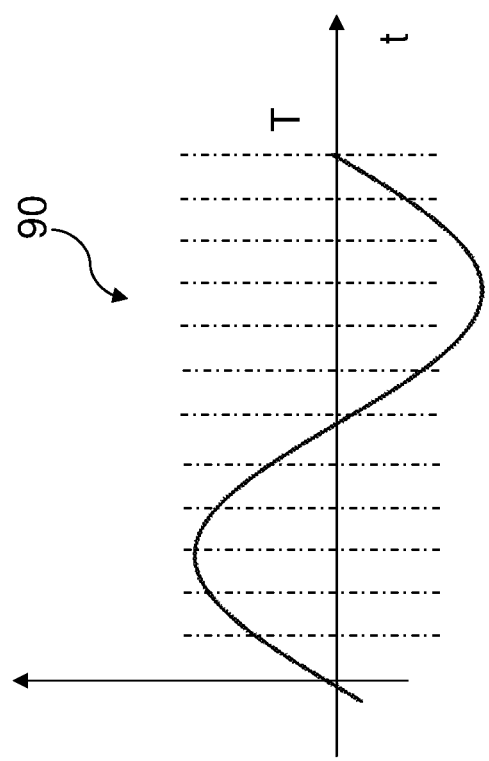
FIG. 2 shows an example of a respiratory cycle.

FIG. 2 shows an example of respiratory cycle 90, where a point of a patient 6, for instance a point of his chest, follows a periodic movement over time. For instance, ordinate of the graph of FIG. 2 represents a vertical coordinate of said point. Abscissa of FIG. 2 is time. This respiratory cycle 90 has a time period T. Time period T is generally comprised between ten and twenty seconds, such as a value equal to fifteen seconds. Time period T can be divided in different temporal phases that could be named respiratory phases. In the example of FIG. 2, time period T of the respiratory cycle 90 is divided in twelve temporal phases. According to other embodiments, time period T of a respiratory cycle 90 is divided in a number of temporal phases that is comprised between ten and fifteen temporal phases. With the method and the imaging system 100 of the disclosure, a CBCT image 15 and a radiograph 25 may be associated to each temporal phase (or respiratory phase) similar to those of FIG. 2.

Figure 3:
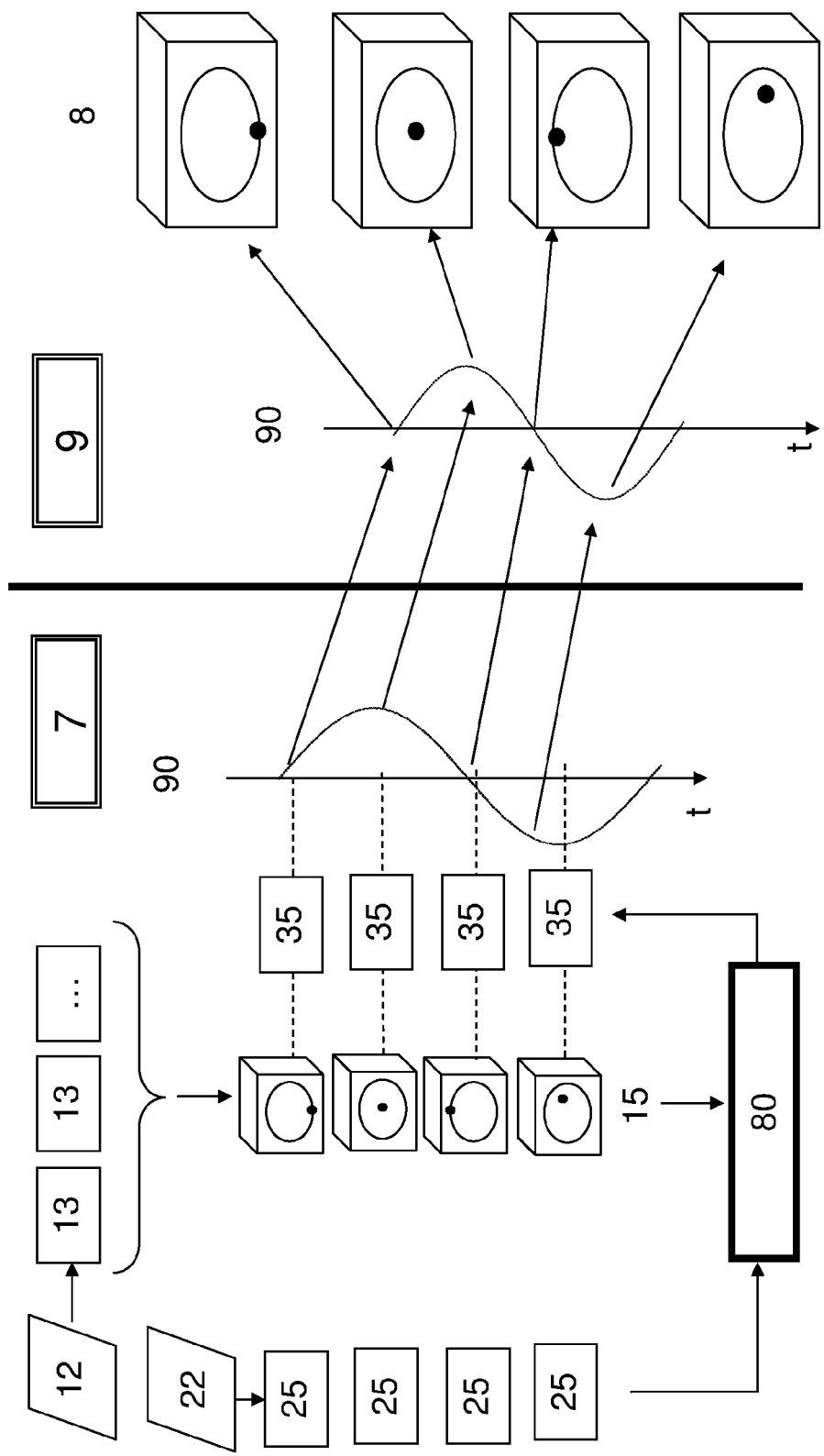
FIG. 3 shows exemplary steps that can be performed before treatment in radiation therapy.

FIG. 3 shows exemplary steps that can be performed before a treatment in radiation therapy. Well before treatment 9, for instance two weeks before treatment, CT images 8 are generated with a 4D-CT apparatus. The different CT images 8 correspond to different temporal phases, for instance to different respiratory phases of a respiratory cycle 90 occurring at a time 'well before treatment 9': see right part of FIG. 3. The arrows refer to different respiratory phases of the respiratory cycle 90 'well before treatment 9'.

Back dot in the CT images 8, whose position varies, is for instance a tumour. From the CT images 8, a treatment plan can be established.

A treatment plan in the context of radiation therapy is known by the one skilled in the art. A treatment plan comprises various physical and geometrical parameters related to the radiation setup that is used that allow obtaining a desired dose distribution in a target volume. A treatment plan is generally determined by a medical physicist, from the knowledge of the desired dose distribution that is imposed generally by a doctor.

Just before treatment 7, a detector 12 of a 4D-CBCT apparatus provides different CBCT scans 13. Exposition time for generating a CBCT scan 13 is generally of the order of ten to twenty milliseconds (ms). From the different CBCT scans 13, a 4D-CBCT apparatus is able to build different CBCT images 15 corresponding to different temporal phases, for instance to different respiratory phases of a respiratory cycle 90 occurring at a time 'just before treatment 7'. The respiratory cycles 90 'well before treatment 9' and 'just before treatment 7' are for instance measured with an external device such as a spirometer, but other techniques could be used. For instance, the two respiratory cycles 90 of FIG. 3 could be determined from an analysis of CT 8 and CBCT 15 images.

Just before treatment 7, a radiographic detector 22 of a radiographic apparatus provides different radiographs 25. Exposition time for generating a radiograph 25 is generally of the order of one hundred ms. The different radiographs 25 are taken at different times. The synchronization device 80 of the imaging system 100 of the disclosure is able to correlate one or more radiographs 25 to one or more CBCT image 15. In the example shown in FIG. 3, each of four radiographs 25 is associated to one of the four CBCT images 15. Each pair comprising one radiograph 25 and one CBCT image 15 corresponds to a given temporal phase, to a given respiratory phase in the example of FIG. 3. From this correlation, one or more reference radiographs 35 can be determined.

For realizing the correlation between a CBCT image 15 and a radiograph 25, the synchronization device 80 can, for instance, read time stamps or time tags associated to the CBCT images 15 and to the radiographs 25, and link a radiograph 25 to a CBCT image 15 if they have same or equivalent time tag. A time tag equivalent to a given time tag is for instance said given time tag +/−time period T of a respiratory cycle 90. According to another example, a time tag is equivalent to another time tag if the absolute value of their difference is lower than a threshold, for instance lower than 10%, or lower than 5%. Other values of such a threshold could be used. Generally, a time stamp or time tag is associated to each CBCT image 15, and to each radiograph 25. Such time tags can be provided for instance by a CBCT apparatus, and by a radiographic apparatus.

According to an embodiment, the synchronization device 80 of the imaging system 100 of the disclosure is able to control a radiographic apparatus for performing a radiographic sequence for generating one or more radiographs 25 correlated to one or more CBCT images 15. For example, knowing that CBCT images 15 correspond to four respiratory phases of a respiratory cycle 90 determined just before treatment 7, the synchronization device 80 controls the radiographic apparatus in order to provide one radiograph 25 for each of said four respiratory phases.

Generally, it is also desired to correlate the temporal phases between the times 'just before treatment 7', and 'well before treatment 9'. In the example of FIG. 3, linking of the two respiratory cycles 90 corresponding to these two times (7, 9) is illustrated by arrows. Then, one can link a CBCT image 15 with a CT image 8. This correspondence can be performed by a CBCT apparatus for instance. According to an embodiment, the synchronization device 80 of the imaging system 100 of the disclosure is able to control the CBCT apparatus to provide CBCT images 15 corresponding to temporal phases equivalent to the temporal phases associated with the CT images 8. Then, the synchronization device 80 may be also able to control to the radiographic apparatus for providing radiographs 25 at same or equivalent temporal phases as the ones of the CBCT images 15. This facilitates later correlation between radiographs 25 and CBCT images 15, for providing the reference radiographs 35.

Once reference radiographs 35 have been determined, comparison with radiographs 25 taken during treatment can be performed. According to a first possible application, position of a tissue, a tumor for instance, can be determined if a radiograph 25 taken during treatment is sufficiently close to a reference radiograph 35 determined just before treatment 7. Indeed, if two such radiographs (25, 35) are so close, that means that the position of a tissue at the time the radiograph 25 during treatment is taken is similar to the position of same tissue at the time stamp associated to the reference radiograph 35. As a CBCT image 15 is associated with a reference radiograph 35, one can easily determine position of the tissue.

According to a second possible application, gating in radiation therapy can be performed from the knowledge of one or more reference radiographs 35. Gating is known by the one skilled in the art. It relates to send a radiating treatment beam to the patient 6 at selected times. For instance, from different CBCT images 15, one could select one or more of said CBCT images 15 for which it is desired to send the treatment beam. Said selected CBCT images 15 correspond for instance at some positions of a tumour for which the treatment beam will reach it with a high probability. As a reference radiograph 35 is associated with a CBCT image 15, one can select one or more reference radiographs 35 corresponding to cases where it is desired to send the treatment beam. During treatment, when a measured radiograph 25 is sufficiently close to a reference radiograph 35, the radiation treatment beam is sent to the patient 6.

Different techniques known by the one skilled in the art could be used for comparing a radiograph 25 taken during treatment with a reference radiograph 35, or for matching a radiograph 25 taken during treatment with a reference radiograph 35. A comparison on a pixel to pixel basis could be performed for instance. Then, it can be concluded, for instance, that a radiograph 25 corresponds to a reference radiograph 35 is there is no difference larger than 10% in pixel intensity, for all pixels. According to another example, one could determine an average difference in pixel intensity between a radiograph 25, and a reference radiograph 35. If said average difference is lower than a threshold, for instance 5% in pixel intensity, one could deduce that the radiograph 25 taken during treatment is similar to the reference radiograph 35.

A technique analog to the one disclosed in "Monitoring tumor motion by real time 2D/3D registration during radiotherapy", by Christelle Gendrin et al. in Radiotherapy and Oncology 102 (2012) 274-280 could also be used for comparing a radiograph 25 taken during treatment with a reference radiograph 35. The content of this whole article is included in this patent application by reference. A technique analog to the one disclosed in "A review of 3D/2D registration methods for image-guided interventions", by Markelj P, Tomazevic D, Likar B, Pernuš F in Med Image Anal 2012; 16:642-61, could also be used for comparing a radiograph 25 taken during treatment with a reference radiograph 35. The content of this whole article is included in this patent application by reference.

The present disclosure has been described in terms of specific embodiments, which are illustrative of the disclosure and not to be construed as limiting. More generally, it will be appreciated by persons skilled in the art that the present disclosure is not limited by what has been particularly shown and/or described hereinabove. Reference numerals in the claims do not limit their protective scope. Use of the verbs "to comprise", "to include", or any other variant, as well as their respective conjugations, does not exclude the presence of elements other than those stated. Use of the article "a", "an" or "the" preceding an element does not exclude the presence of a plurality of such elements.

The disclosure can also be summarized as follows. Imaging system 100 comprising: a 4D-CBCT apparatus able to generate a plurality of CBCT images 15 corresponding to different temporal phases, a radiographic apparatus able to generate a radiograph 25, and a synchronization device 80 for correlating (or linking) a radiograph 25 of said radiographic apparatus with a CBCT image 15 generated by said 4D-CBCT apparatus, such that a reference radiograph 35 can be determined.

The invention claimed is:

1. A method for determining a reference radiograph, comprising the steps of:
   providing a Four-Dimensional Cone Beam Computed Tomography (4D-CBCT) apparatus, comprising a source and a detector configured to be selectively positioned at different angular positions around a patient, the 4D-CBCT apparatus generating a plurality of CBCT images corresponding to different times;
   providing a radiographic apparatus comprising a radiographic source and a radiographic detector, the radiographic apparatus being configured to generate a sequence of radiographs corresponding to different times;
   positioning a patient for generating CBCT images of the patient with the 4D-CBCT apparatus and radiographs of the patient with the radiographic apparatus;
   performing a 4D-CBCT scanning sequence with the 4D-CBCT apparatus to generate a plurality of CBCT images of a portion of the patient's body, the CBCT images corresponding to different temporal phases associated with the patient;
   performing a radiographic sequence with the radiographic apparatus so as to generate a plurality of first radiographs of patient, the first radiographs corresponding to different temporal phases associated with the patient;
   providing a synchronization device configured to correlate a CBCT image corresponding to a given temporal phase with a radiograph corresponding to an equivalent temporal phase;
   generating a correlated radiograph by correlating, with the synchronization device, one of the first radiographs with a designated one of the CBCT images, the designated CBCT image corresponding to a designated temporal phase; and
   identifying the correlated radiograph as the reference radiograph.

2. A method according to claim 1, wherein the radiographic sequence is performed during at least a portion of the 4D-CBCT scanning sequence.

3. A method according to claim 1, wherein the temporal phases correspond to respiratory phases of a respiratory cycle.

4. A method according to claim 1, wherein each of the CBCT images corresponds to a CT image generated previously by a CT apparatus.

5. A method according to claim 1, wherein correlating with the synchronization device comprises correlating the first radiographs with the CBCT images in multiple reference radiographs, wherein each of the multiple reference radiographs corresponds to a given designated temporal phase.

6. A method according to claim 5, wherein comprising the step of generating at least ten CBCT images corresponding to at least ten temporal phases from the 4D-CBCT scanning sequence.

7. A method according to claim 1, comprising the step of generating, from the radiographic sequence, at least ten radiographs for at least ten temporal phases from the radiographic sequence.

8. A method according to claim 1, further comprising the steps of:
   positioning a target volume of the patient's body between the radiographic source and the radiographic detector;
   generating a second radiograph of the target volume with the radiographic apparatus;
   comparing the second radiograph with the reference radiograph to generate a comparison result;
   determining, based on the comparison result, whether the second radiograph matches the reference radiograph; and
   when the second radiograph matches the reference radiograph, determining a position of a tissue of the patient from the CBCT image correlated with the reference radiograph.

9. A method according to claim 1, wherein when the reference radiograph corresponds to a given temporal phase in order to send the treatment beam, the method further comprises the steps of:
   configuring the radiographic apparatus to generate an image of a patient's body during treatment;
   positioning a target volume of the patient's body in a treatment position;
   generating a second radiograph of the target volume with the radiographic apparatus;
   generating a comparison result by comparing the second radiograph with the reference radiograph;
   determining, based on the comparison result, whether the second radiograph matches the reference radiograph; and
   sending the treatment beam to the patient if the second radiograph matches the reference radiograph.

10. An imaging system for identifying a reference radiograph for use in radiation therapy, the imaging system comprising:
   a 4D-CBCT apparatus comprising a source and a detector configured to be selectively positioned at different angular positions around a patient, the 4D-CBCT apparatus generating a plurality of CBCT images corresponding to different times;
   a radiographic apparatus, including a radiographic source and a radiographic detector, the radiographic apparatus being configured to generate a sequence of radiographs corresponding to different times; and a synchronization device configured to generate a reference radiograph by correlating a CBCT image corresponding to a given temporal phase with a radiograph corresponding to an equivalent temporal phase.

11. An imaging system according to claim 10, wherein:
generating the CBCT images comprises generating the CBCT images as three dimensional images;
generating the radiographs comprises generating the radiographs as two dimensional images.

12. An imaging system according to claim 10, wherein the temporal phase corresponds to a respiratory phase of a respiratory cycle.

13. An imaging system according to claim 10, wherein the synchronization device comprises a controller configured to control the radiographic apparatus to generate the reference radiograph.

14. An imaging system according to claim 13, wherein the controller is further configured to generate the radiograph by controlling the radiographic apparatus to perform a radiographic sequence during at least a portion of a 4D-CBCT scanning sequence the radiograph.

15. An imaging system according to claim 10, wherein the synchronization device is configured to determine a temporal phase of a CBCT image.

* * * * *